(12) United States Patent  
Spector

(10) Patent No.: US 6,520,826 B2
(45) Date of Patent: Feb. 18, 2003

(54) PLUSH FRAGRANCING SYSTEM

(76) Inventor: Donald Spector, 380 Mountain Rd., Union City, NJ (US) 07087

( * ) Notice: Subject to any disclaimer, the term of this patent is extended or adjusted under 35 U.S.C. 154(b) by 0 days.

(21) Appl. No.: 09/797,335

(22) Filed: Mar. 1, 2001

(65) Prior Publication Data

US 2002/0123295 A1 Sep. 5, 2002

Related U.S. Application Data

(60) Provisional application No. 60/271,397, filed on Feb. 27, 2001.

(51) Int. Cl.⁷ .............................................. A63H 3/00
(52) U.S. Cl. ........................ 446/73; 446/72; 446/369; 446/385; 239/60
(58) Field of Search ............................. 446/385, 369, 446/268, 491, 71–73; 119/707, 711; 239/60

(56) References Cited

U.S. PATENT DOCUMENTS

| | | | | |
|---|---|---|---|---|
| 1,767,911 A | * | 6/1930 | Berko et al. ................... | 446/74 |
| 2,618,892 A | * | 11/1952 | Locks et al. ................. | 446/268 |
| 3,955,314 A | * | 5/1976 | Robb .......................... | 446/268 |
| 4,419,395 A | * | 12/1983 | Sugimoto ................... | 446/385 |
| 4,889,284 A | * | 12/1989 | Spector ...................... | 239/211 |
| 5,316,182 A | * | 5/1994 | Lee et al. ................... | 446/475 |
| 5,676,583 A | * | 10/1997 | Wang et al. ................. | 446/268 |
| 5,797,208 A | * | 8/1998 | Lessa ............................... | 43/2 |
| 6,089,947 A | * | 7/2000 | Green ......................... | 446/268 |

* cited by examiner

Primary Examiner—Jacob K. Ackun
Assistant Examiner—Bena B. Miller
(74) Attorney, Agent, or Firm—Lieberman & Nowak, LLP

(57) ABSTRACT

A fragrance dispensing device suitable for incorporation into a plush figure. In one of the preferred embodiments of this invention, the fragrance dispensing device comprises a hollow body in the form of a sphere or a ball having a slit valve or a one-way valve disposed within the wall of the hollow body. A scented cartridge is inserted into the hollow body through the valve or some other resealable opening in the hollow body. In the preferred embodiments of this invention, the fragrance dispensing device is encompassed within an appendage or the head of a stuffed animal figure. Once the hollow is charged with the fragrance cartridge, it can be compressed so as to force a discrete charge of scented air from within the hollow body, into its surrounding core material which make the filler of the stuffed animal figure. The amount of fragrance dispensed from within the hollow body is based, in part, upon the volume of the hollow body and the partial pressure of the fragrance within the cartridge. Thus, if the fragrance is highly volatile, more fragrance will be present in the discrete charge emitted from the hollow body. Where additional scent is desired, the hollow body can be repeatedly compressed to discharge additional discrete charges of fragrance into the environment.

5 Claims, 5 Drawing Sheets

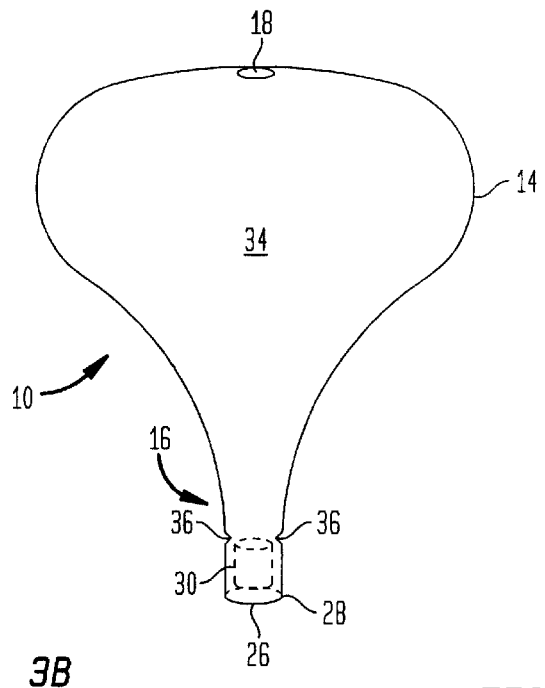
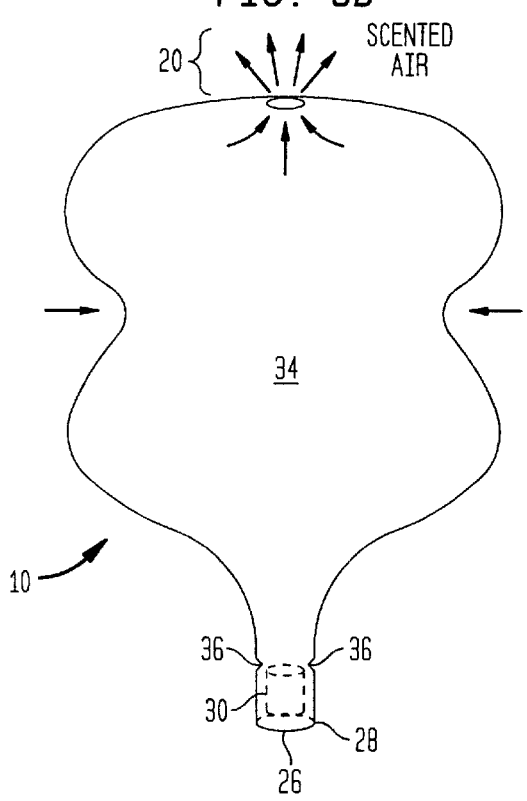
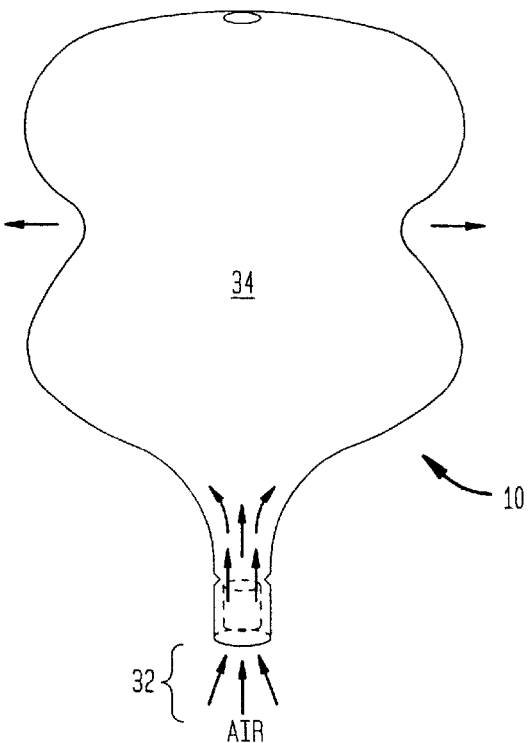

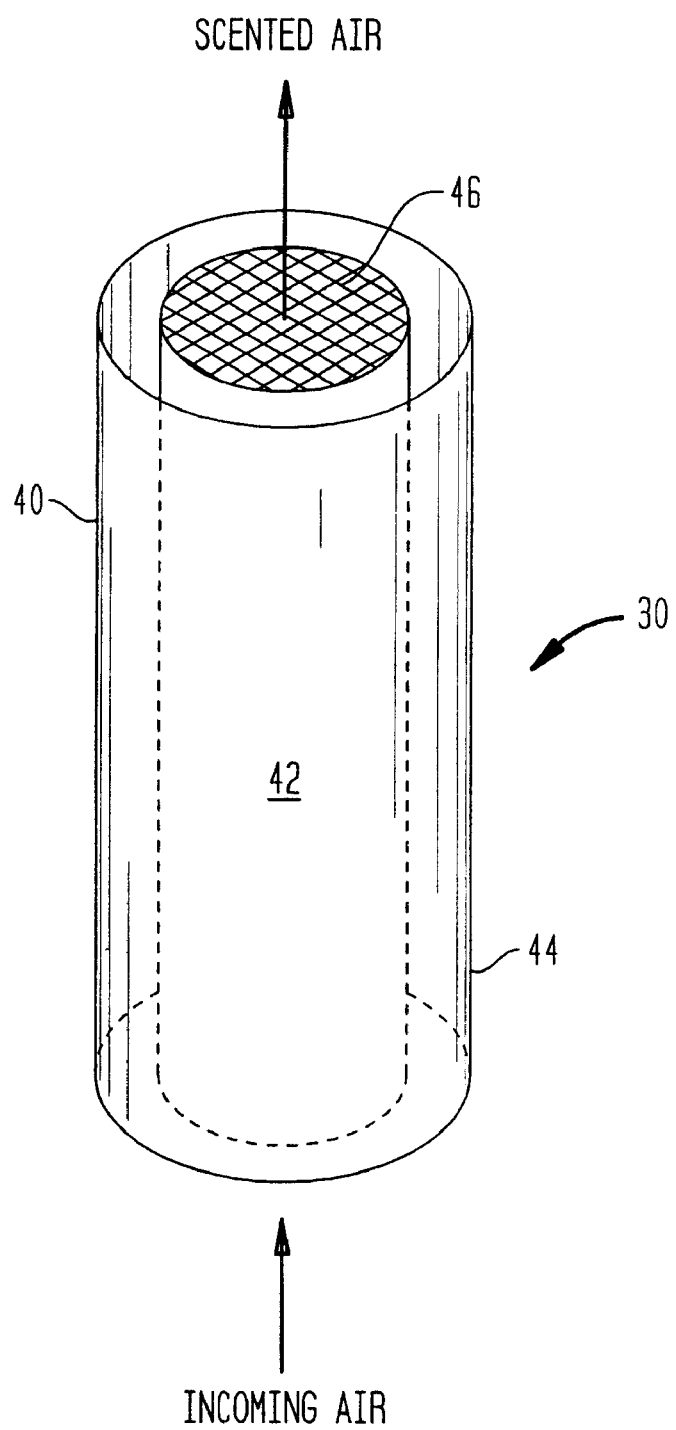

PLUSH FRAGRANCING SYSTEM

CROSS-REFERENCE TO RELATED APPLICATIONS

This application is based on Provisional Patent Application entitled Plush Fragrancing System, Ser. No. 60/271,397, filed Feb. 27, 2001.

BACKGROUND OF THE INVENTION

1. Field of the Invention

This invention relates to fragrance dispensing devices. More specifically, this invention relates to a plush figure (e.g. stuffed animal) having a fragrance dispensing device isolated within its body The fragrance is dispensed in accordance with the method of this invention by causing a discrete charge of scented air to be displaced from within a resilient deformable chamber located within the figure. The discrete charge is contacted with a core material within the plush figure, and, thereafter, permeates through the surface covering of the figure into the environment surrounding the plush figure.

2. Description of the Prior Art

The process of dispensing of perfumes, scented fluids and solid air fresheners from various contrivances is well-know. Generally, such processes involve aspirating a finite charge of scented liquid from a reservoir, or alternatively, allowing a scented liquid or solid to passively evaporate/sublime into the atmosphere at a known or controlled rate.

The following patents are representative of devices which utilize one or more of the above processes for dispensing a scent into the ambient environment.

U.S. Pat. No. 6,089,947 (to Green, issued Jul. 18, 2000) discloses an air freshener representing a figure, such as an animal, cartoon character, or other form having a body and a mouth. The body of the Green air freshener is made of an air-permeable material (e.g. plush fabric) and forms an internal cavity within the body. A mouth leads through the body and into the internal cavity so that a scented pellet can be inserted through the mouth and retained within the internal body cavity. The scented pellet then releases a permeating scent to the ambient or surrounding air. Once spent, fresh pellets can be added through the mouth of the figure.

U.S. Pat. No. 4,889,284 (to Spector, issued Dec. 26, 1989) discloses a rechargeable air freshener in a figurative form that includes a body and a head section, and an outer casing of permeable fabric material whose contours define all sections of the figure. The interior of the casing and all sections thereof are stuffed with a compressible core of absorbent material having good wicking properties, the core rendering the figure soft and squeezable. Occupying an internal cavity in the core, which extends from the body to the head section thereof, is a fragrance dispenser comprising a cylindrical can filled with liquid fragrance, a depressible stem projecting from one end of the can terminating in an actuator head provided with a spray nozzle. The can is so placed in the cavity that the actuator head lies just below the scalp region of the head section of the casing. When, therefore, the user presses the scalp region of the figure, this actuates the dispenser to spray a mist of liquid fragrance onto the core material within the head section, the fragrance being absorbed thereby and thereafter wicked throughout the core. The aromatic vapor is volatilized from the outer surface of the core, passes through the permeable casing and, thus, released into the atmosphere.

As is evident from the above discussion of the representative prior art, each of the foregoing fragrance dispensers require either the periodic insertion of a fragrance releasing sachet or pellet, or alternatively, the replenishment of a reservoir containing a scented liquid. In the case of the Green device discussed above, the scent is continuously released into the atmosphere until exhausted and replenished. Thus, the amount of scent present in ambient environment is independent of any control that can be exercised by the user. In the case of the Spector device, his fragrance dispensing system combines a traditional scent aspiration system with the modulating effect of the plush figure, to both limit the amount of scent that is dispensed into the atmosphere at one time and yet extend the effect thereof through an intermediate medium which comprises core material of the plush figure. In the Spector device, the recharging of the fluid reservoir containing the liquid fragrance is more cumbersome than in Green, notwithstanding its apparent advantages. Accordingly, there continues to exist a need for a fragrance dispensing figure having the favorable attributes of Spector device, with the ease of replenishment of the fragrance source of the Green device.

OBJECTS OF THE INVENTION

It is the object of this invention to remedy the above as well as related deficiencies in the prior art.

More specifically, it is the principle object of this invention to provide an improved fragrance dispensing device including means for dispensing a discrete charge of fragrance from a reservoir that can be readily replaced or replenished.

It is another object of this invention to provide an improved fragrance dispensing device in the form of a plush figure wherein a discrete charge of fragrance is dispensed from a source within the figure by simply compressing a flexible container within the figure.

It is still yet another object of this invention to provide an improved fragrance dispensing device in the form of a plush figure wherein a discrete charge of fragrance is dispensed into the body of the figure from a scented cartridge having concentrated fragrance adsorbed upon a solid carrier material.

SUMMARY OF THE INVENTION

The above and related objects are achieved by providing a fragrance dispensing system and device comprising a compressible, resilient hollow body having a cartridge with a concentrated fragrance adsorbed on a solid, porous carrier. In the preferred embodiments of this invention, the hollow body can be in the form of a sphere or a ball having a slit or valve. The cartridge is inserted into the hollow body through the valve or some other resealable opening in the hollow body. Once the sphere is charged with the fragrance cartridge, it can be compressed so as to force a discrete charge of scented air from within the hollow body, into its surrounding environment. The amount of fragrance dispensed from within the hollow body is based, in part, upon the volume of the hollow body and the partial pressure of the fragrance within the cartridge. Thus, if the fragrance is highly volatile, more fragrance will be present in the discrete charge released from the hollow body. Where additional scent is desired, the hollow body can be repeatedly compressed to discharge additional discrete charges of fragrance into its immediate environment.

In order to prolong the effect of such dispenser, the hollow body is preferably embedded within the body of a plush figure. The hollow body can be strategically placed in the plush figure's tummy, head or a squeezable appendage. The shape of the hollow body will, thus, conform in overall dimension with its intended situs within the plush figure.

The advantages of the fragrance dispensing system of this invention include the ability to recharge the system by simply replacing the fragrance dispensing cartridge in the hollow body, or by totally replacing the entire hollow body with a new one having a fresh fragrance dispensing cartridge. The system also has the advantage of isolating the source of the fragrance from direct contact with fabrics and similar materials that can be wetted and/or stained and/or discolored by contact with the fragrance. Moreover, the replenishment of the system does not involve, nor require, the use of liquids which are cumbersome and difficult to handle, particularly in the context of refilling of a tiny reservoir.

BRIEF DESCRIPTION OF DRAWINGS

FIG. 3 depicts a fragrance dispensing device of this invention having a resilient compressible chamber suitable for placement within the plush animal figure of FIGS. 1 & 2.

FIG. 4 depicts an enlarged view of a cartridge suitable for use in a fragrance dispensing device of this invention.

DETAILED DESCRIPTION OF THE INVENTION INCLUDING PREFERRED EMBODIMENTS

Figure 1:
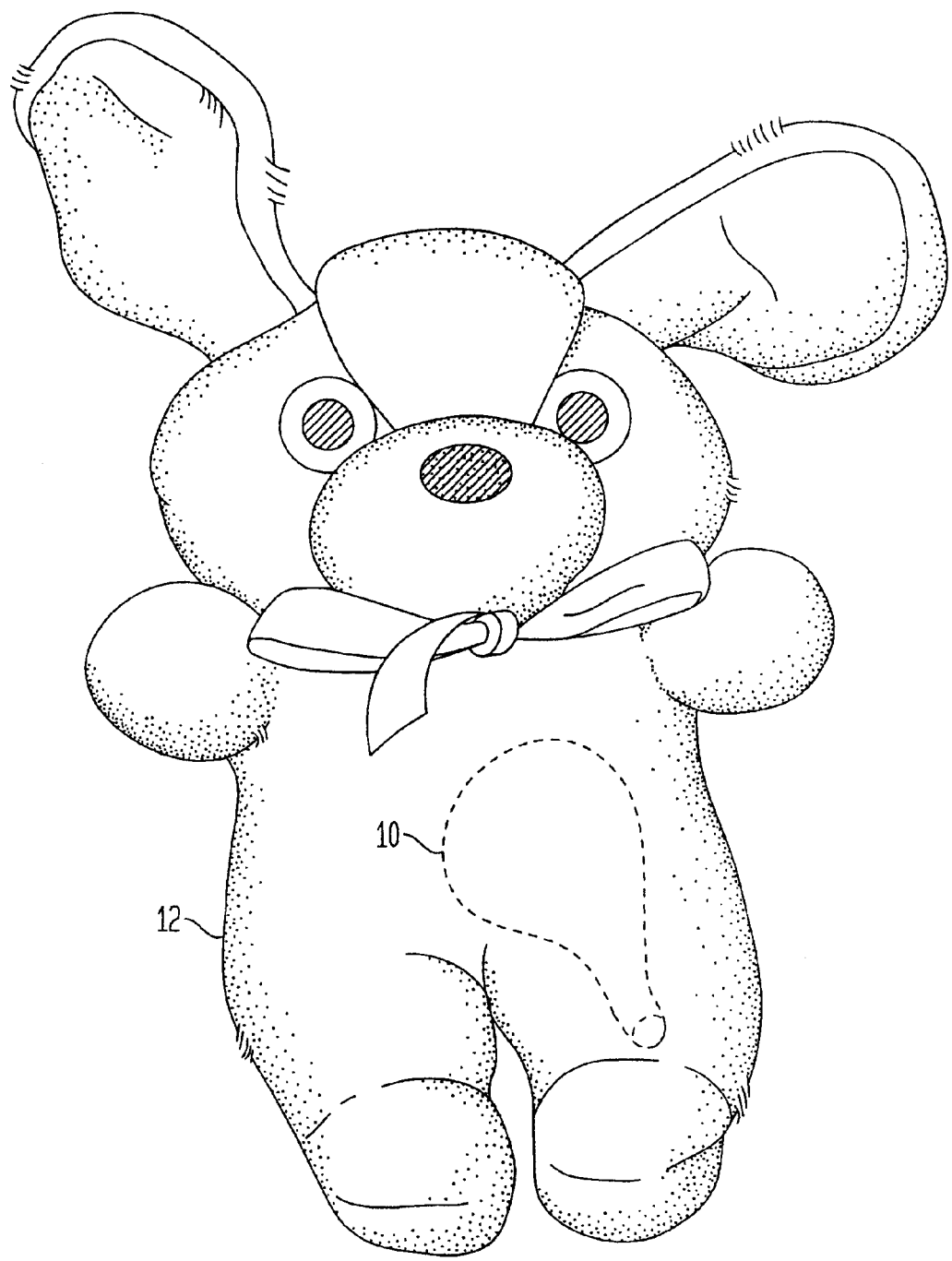
FIG. 1 depicts a frontal view of a plush animal figure in the form of a rabbit.

The fragrance dispensing system and device of this invention comprises a resilient, compressible hollow body having a cartridge, or a similar dispenser, having a concentrated fragrance adsorbed onto a porous solid support (e.g. sponge). The compressible hollow body, suitable for use in the system of this invention can be in the form of a sphere or globe. The compressible hollow body defines a chamber having a scented dispenser disposed therein. The hollow body is further provided with a simple valve which is normally in the closed or sealed position until the hollow body is compressed. The exertion of compressive forces on the hollow body cause displacement in the wall of the globe and thereby the opening of the valve. Where a discrete charge of fragrance is present within the chamber, such compression cause discharge of the discrete charge from within the internal chamber defined by the hollow body. The hollow body is preferable provided with an additional one way valve to permit air to enter the internal chamber of the hollow body upon the release of the compressive pressure, thus, re-filling the globe with air. In the preferred embodiments of this invention, air entering the internal chamber of the hollow body is caused to impinge or flow over the dispenser contained therein, and, thus, is combined with fragrance from the dispenser. This process can be repeated, and additional scented air discharged from the internal chamber of the hollow body. It is noted and emphasized that only so much of the fragrance as can be accommodated by the volume of air within the internal chamber is discharged with each compression of the hollow body. This configuration, thus, permits precise control over the amount of scent that is dispensed from the dispenser and greatly extends the useful life of the dispenser, while at the same time preventing overwhelming the surroundings with scented air. In a preferred embodiment the dispenser is in the form of a cartridge as described below.

In order to further control this process, the fragrance dispensing system includes the a plush figure that is filled with an inert fibrous core. The plush figure can be of the type and configuration described in commonly assigned U.S. Pat. No. 4,889,284 (to Spector, issued Dec. 26, 1989), which is herein incorporated by reference in its entirety. In the plush figure described in commonly assigned Spector '284 patent, the scent is dispensed by aspiration of a liquid spray from a fluid reservoir within the plush figure onto a core material in the body of the plush figure. The aspirated liquid spray is absorbed onto the core material which transports the liquid, by capillary action, throughout the core of the animal figure, and to the permeable surface covering of the plush figure. The core material, to be effective in this environment is preferably comprised of a synthetic, nonporous fiber, that is essentially inert and hypoallergenic. In the context of this invention, the core material provides a comparable function to a passive scent dispensing medium—namely, its provides a high surface area medium for effecting diffusion and exchange of a defined volume of air and fragrance between the core of the plush figure and the environment external to the plush figure. As is appreciated, this dispensing of a discrete charge of fragrance from the fragrance dispensing cartridge of the compressible hollow body within the plush figure provides not only precise control over the amount of fragrance that is contained within each charge of scented air, but also isolates the fragrance dispensing cartridge so as to prevent passive diffusion of fragrance from the cartridge. Thus, the unique fragrance dispensing system of this invention not only extends the useful life of the cartridge, but also prevents the release and/or dispensing of an excessive amount of fragrance into the ambient environment. The core material of the plush figure also cooperates in this regard, by retaining a residual scent that can gradually be evolved where the plush figure itself is in an environment that causes air flow over the exterior surface of the figure. Thus, long after the discrete charge of the fragrance has been dispensed from the compressible hollow body within the plush figure, the core of the figure provides an intermediate mechanism for continuous, metered release of fragrance though the surface of the plush figure.

Figure 2:
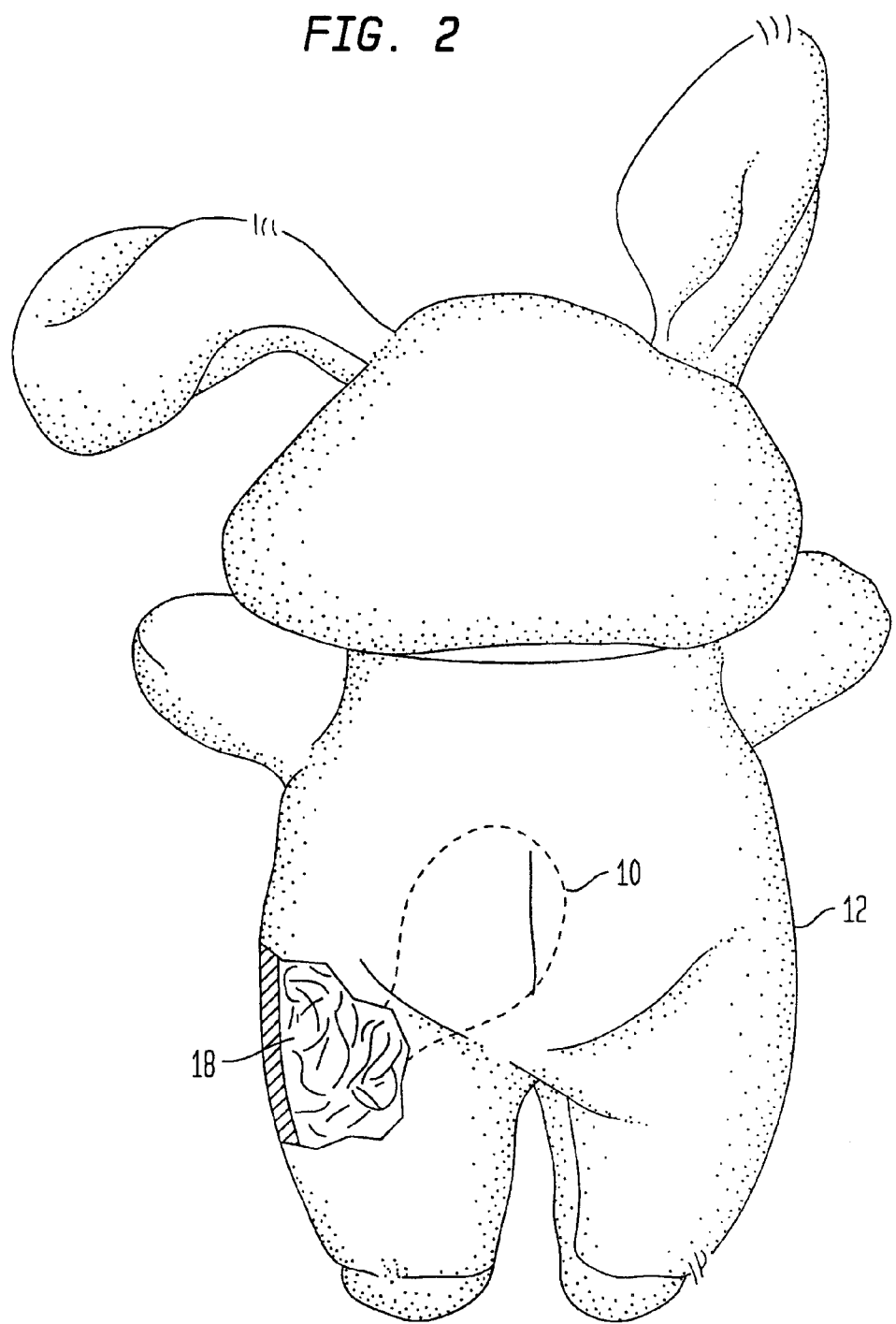
FIG. 2 depicts a rear view of a plush animal figure in the form of a rabbit, with a partial cutaway exposing core material stuffing of its left leg.

In the embodiments of the invention illustrated in FIGS. 1 & 2, a hollow compressible body (10) is positioned within the lower body and extremity of the plush figure (12). As shown in FIG. 3, the hollow compressible body (10) can be in the form of a pear shaped form having an essentially bulbous head (14) and an elongate tube (16), each of the head (14) and tube (16) having a one way valve (18, 26) positioned at each end thereof. As more completely illustrated in FIG. 3, the hollow compressible body (10) includes a one way discharge valve (18) on the proximal end (14) thereof. Upon compression of the compressible body, a discrete charge of fragrance (20) is dispensed into the core of the plush figure (12). The distal end of the elongate tube (16) also includes a one-way inlet valve (26) and a removal cap (28). The ability to remove the cap from the distal end of the tube allows for access to the chamber (30) in such tube and thereby the insertion and replacement of an in-line cartridge, or similar dispenser, within the hollow cavity of the tube (16). The one-way inlet valve (26) in the removable cap (28) allows for air to enter the elongate tube and thereby pass through the cartridge within the tube and thereafter into the hollow cavity at the proximal end of the compressible body. Accordingly, when the proximal end (14) of the compressible body is compressed, as illustrated in FIG. 3B, scented air (20) contained therein is discharged into the core of the plush figure (12). Upon release of such compression, as illustrated in FIG. 3C, a negative pressure is created within the chamber (34). This negative pressure causes fresh air (32) to be drawn into the distal end of the tube (16) through the one-way inlet valve (26) located in the cap (28) on the distal end of the tube. As air (32) flows into the tube (16), it is channeled into the cartridge (30), where it impinges upon a solid support having the concentrated fragrance. Such contact causes a finite amount of fragrance to combine with the air and fill the chamber (34) located in the proximal end (14) of the compressible body (10).

The fragrance dispensing cartridge, or similar dispenser (30) can take many forms and include one or more combinations of scents. In the embodiment of the invention illustrated in FIG. 4, the cartridge comprises a cylindrical housing (40) having a central channel (42) defined by a porous material (44), in the form or(a plastic foam or sponge like material ) The foam is essentially inert relative to the concentrated fragrance that is adsorbed onto its surface and within the bibulous matrix thereof The porous material (44) is retained within the channel (42) of the cartridge (30) by a screen or mesh (46), so as to permit incoming air to impinge upon such porous material.

Fragrance dispensing cartridges of the type suitable for use in this invention are disclosed in U.S. Pat. No. 4,523,870, which is herein incorporated by reference in its entirety. The porous material can also include other agents to stabilize the fragrance concentrate, or otherwise control its release from the medium. The overall dimensions of the fragrance dispensing cartridge is dictated by the shape of the cavity in which it is to be placed. For example, where the fragrance dispensing cartridge is used in the configuration of the device illustrated in the Figures accompanying this application, it is preferably in the form of a cylinder having an opening on each end thereof. Thus, it can be inserted into the distal end of the elongate tube, and positioned in-line with the direction for passage of air from one the distal end of the tube to the proximal end of the compressible chamber. When air is directed through the cartridge it contacts and the carrier surface of the cartridge having absorbed fragrance concentrate. In this process, fragrance concentrate is once again combined with the air stream and flows into the proximal end of the compressible body, so as replenish the device with another "discrete charge" of scented air.

In order to retain the fragrance dispensing cartridge in position within the elongate tube (16), retainer means (36) can be provided either within the distal end of the tube (16), or on the interior surface of the removable cap (28), or on both. More specifically, the interior of the distal end of the elongate tube (16) is also provided with a constriction or restriction means (36) to secure the cartridge (30), in-line, in the distal end of such tube. Thus, upon compression of the proximal end (14) of the compressible body (10), a discrete volume of scented air (20) is discharged from the interior chamber (34) thereof through the one-way dispensing valve (18) in the proximal end (14) of the compressible body (10) into the core (18) of the plush figure (12). Upon relaxation of the compressive forces upon the compressible body (10), the compressible chamber (34) returns to its normal/original position. In the course of this sequence, a negative pressure is created within the compressible chamber, so as to draw fresh air (32) from the environment, external to the plush figure, through the one-way inlet valve (26) in the removal cap (28) on the distal end of the tube (16). The air (32) entering through the one-way inlet valve (26) in the cap is directed, through the in-line, cartridge (30), wherein it causes concentrated fragrance from the cartridge to mix with the in-coming fresh air, so as to once again charge the compressible chamber (34) with a discrete amount of fragrance. This process can be repeated over an over again until the concentrated fragrance in the cartridge is consumer/exhausted. The end-cap (28) on the distal end of the elongated tube (16) can then be removed, the exhausted fragrance dispensing cartridge replace with a new in-line fragrance dispensing cartridge. The ability to replace the cartridge provides versatility in the number of different fragrances that can be used with the same plush figure. Access to the removal cap (26) is through a flap (not shown) in the pad of the left foot of the plush figure (12), or in any other convenient location. Thus, the flap is simply peeled back, the cap removed from the distal end of the tube. The spent cartridge is thereafter removed from the opened tube and new cartridge inserted. The cap is then replaced, and the flap of plush material closed.

Figure 5A:
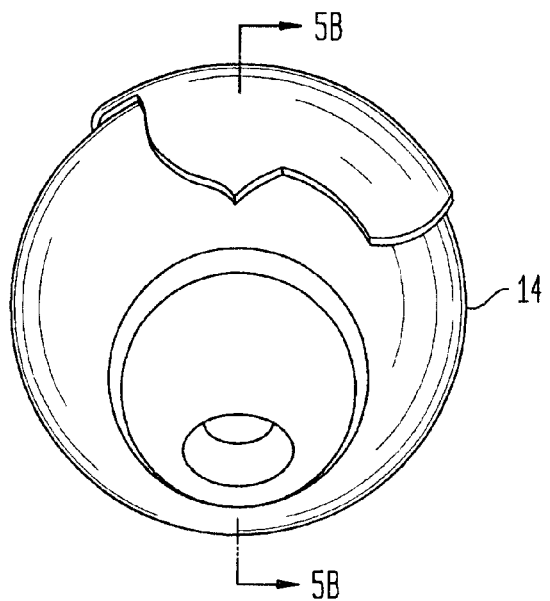
FIG. 5 is a second embodiment of a dispensing device.
Figure 5B:
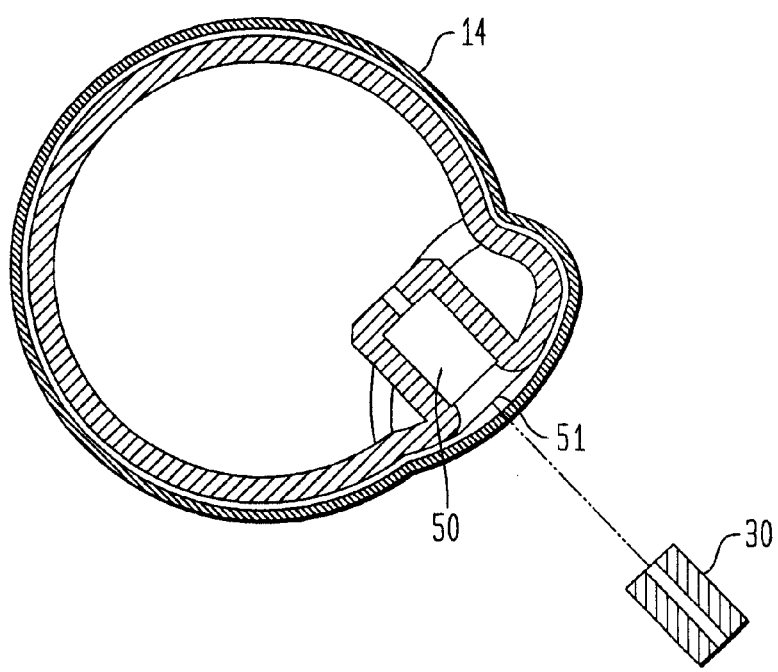

A second embodiment of a fragrance dispenser is shown in FIG. 5. In FIG. 5, the compressible body 14 is in the shape of a ball. Cartridge 30 fits into recess 50 and secured with outer plug 51.

Additional modifications to the preferred embodiments of the invention include the placement of the hollow compressible body in the head or belly of the plush figure. The form or shape of the hollow compressible body would, where practical, conform to the plush figure form, and otherwise provide access to the fragrance dispensing cartridge to removal or replacement. As noted above, it may be cost effective or desirable to simple replace the entire hollow compressible body; and, in such instance, the plush figure would include means for access and removal of the entire hollow compressible body.

What is claimed is:

1. In a fragrance dispensing device comprising a plush figure having an inert core material and a source of fragrance concentrate housed within said core material, the improvement comprising:

a fragrance dispensing device suitable for incorporating within the plush figure comprising a compressible hollow body having (1) a resilient structure (2) a one-way inlet valve opening through a wall of said hollow body for permitting passage of air into a chamber of said body, (3) at least one one-way pressure release dispensing valve opening through the wall of said hollow body for permitting the passage of a fluid vapor from said chamber, upon exertion of a compressing force upon said figure and a fragrance dispenser having fragrance concentrate, absorbed on a replaceable solid porous medium, within said chamber of said hollow body of said device;

with the proviso that at least some of said air entering said chamber comes in contact with said solid porous medium of said fragrance dispenser and thereby effect mixing of at least some of said fragrance concentrate with said air to form a discrete fragrance charge within said chamber.

2. The fragrance dispenser device of claim 1, wherein said fragrance dispenser is a cartridge.

3. The fragrance dispensing device of claim 2, wherein said cartridge includes a housing, a fragrance concentrate absorbed onto a porous material within said housing, and means for directing contact of air with said porous material.

4. The fragrance dispensing device of claim 1, wherein the compressible hollow body comprises an elongate form corresponding to an appendage or a head of the plush figure, and is further characterized as having a proximal or fragrance dispensing end and a distal or air intake end.

5. The fragrance dispensing device of claim 4, wherein the elongate form of the compressible hollow body includes on its distal end, a re-sealable means for opening and closing said chamber of said hollow body, and means for positioning a cartridge, having a fragrance concentrate within said distal end of said chamber, so as to effect mixing of said air with said fragrance concentrate as said air is draw through said at least one one-way pressure release dipensing valve in said distal end and into said chamber.

* * * * *